(12) United States Patent
Lee

(10) Patent No.: US 11,287,374 B2
(45) Date of Patent: Mar. 29, 2022

(54) APPARATUS AND METHOD FOR UPDATING BIOINFORMATION ESTIMATION MODEL

(71) Applicant: SAMSUNG ELECTRONICS CO., LTD., Suwon-si (KR)

(72) Inventor: June Young Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 213 days.

(21) Appl. No.: 16/805,938

(22) Filed: Mar. 2, 2020

(65) Prior Publication Data

US 2020/0378890 A1    Dec. 3, 2020

(30) Foreign Application Priority Data

May 29, 2019    (KR) .......................... 10-2019-0062870

(51) Int. Cl.

| | |
|---|---|
| *G01J 5/02* | (2006.01) |
| *G01N 21/359* | (2014.01) |
| *A61B 5/145* | (2006.01) |
| *G01N 21/3577* | (2014.01) |
| *A61B 5/15* | (2006.01) |

(52) U.S. Cl.
CPC ....... *G01N 21/359* (2013.01); *A61B 5/14532* (2013.01); *A61B 5/150022* (2013.01); *G01N 21/3577* (2013.01); *G01N 2201/1296* (2013.01)

(58) Field of Classification Search
CPC ............ G01N 21/359; G01N 21/3577; G01N 2201/1296; G01N 2201/12746; G01N 21/35; G01N 21/4738; A61B 5/14532; A61B 5/150022; A61B 5/1455; A61B 5/681; A61B 5/7275; A61B 5/0024; A61B 5/0059; A61B 5/145; G16H 50/50
See application file for complete search history.

(56) References Cited

U.S. PATENT DOCUMENTS

| | | |
|---|---|---|
| 5,446,681 A | 8/1995 | Gethner et al. |
| 5,592,402 A | 1/1997 | Beebe et al. |
| 6,107,631 A | 8/2000 | He |
| (Continued) | | |

FOREIGN PATENT DOCUMENTS

| | | |
|---|---|---|
| JP | WO2008133097 A1 | 11/2008 |
| JP | 2016206244 A | 12/2016 |
| WO | 2016142692 A1 | 9/2016 |

OTHER PUBLICATIONS

Blank et al., "Clinical results form a non-invasive blood glucose monitor," SPIE Proceedings, vol. 4624, 10 pages. (Year: 2002).*

*Primary Examiner* — Kiho Kim
(74) *Attorney, Agent, or Firm* — Sughrue Mion, PLLC

(57) ABSTRACT

An apparatus for updating a bio-information estimation model according to an aspect of the invention includes: a data obtainer, which in response to a bio-information estimation model not being valid, is configured to obtain in vivo updating spectra measured during a predetermined period of time from a time when it is determined that the bio-information estimation model is not valid; and a processor configured to determine validity of the bio-information estimation model, and to update the bio-information estimation model using the obtained in vivo updating spectra and in vivo spectra used for generating the bio-information estimation model.

20 Claims, 7 Drawing Sheets

(56) References Cited

U.S. PATENT DOCUMENTS

| | | |
|---|---|---|
| 8,239,052 B2 | 8/2012 | Itoyama et al. |
| 2008/0146899 A1 | 6/2008 | Ruchti et al. |
| 2010/0094578 A1 | 4/2010 | Schneider et al. |
| 2010/0131086 A1 | 5/2010 | Itoyama et al. |
| 2012/0065948 A1 | 3/2012 | Tan et al. |
| 2014/0309756 A1 | 10/2014 | Trygstad |
| 2017/0079565 A1* | 3/2017 | Choi .................... A61B 5/1495 |
| 2017/0319185 A1* | 11/2017 | Choi ................. A61B 5/14532 |
| 2018/0047553 A1 | 2/2018 | Richardson et al. |

* cited by examiner

APPARATUS AND METHOD FOR UPDATING BIOINFORMATION ESTIMATION MODEL

CROSS-REFERENCE TO RELATED APPLICATION(S)

This application claims priority from Korean Patent Application No. 10-2019-0062870, filed on May 29, 2019, in the Korean Intellectual Property Office, the disclosure of which is incorporated herein by reference in its entirety.

BACKGROUND

1. Field

Apparatuses and methods according to example embodiments relate to updating a bio-information estimation model.

2. Description of the Related Art

Diabetes is a chronic disease that causes various complications and can be hardly cured, such that people with diabetes are advised to check their blood glucose regularly to prevent complications. In particular, when insulin is administered to control blood glucose, the blood glucose levels have to be closely monitored to avoid hypoglycemia and control insulin dosage. An invasive method of finger pricking is generally used to measure blood glucose levels. However, while the invasive method may provide high reliability in measurement, it may cause pain and inconvenience as well as an increased risk of disease infections due to the use of injection. Recently, research has been conducted on methods of non-invasively measuring blood glucose by using a spectrometer without blood sampling.

SUMMARY

One or more example embodiments provide an apparatus and method for updating a bio-information estimation model without using bio-information values measured by an invasive method.

According to an aspect of an example embodiment, there is provided an apparatus for updating a bio-information estimation model, the apparatus including: a memory configured to store the bio-information estimation model; and a processor configured to determine whether the bio-information estimation model is valid, obtain in vivo updating spectra which are measured starting when the bio-information estimation model is determined as not being valid, update the bio-information estimation model based on the in vivo updating spectra, and training in vivo spectra that are used for generating the bio-information estimation model.

The apparatus may further include: a spectrometer configured to measure in vivo estimation spectra; wherein the processor is further configured to obtain residual spectra from the in vivo estimation spectra, and determine whether the bio-information estimation model is valid by analyzing the residual spectra.

The processor may be further configured to determine whether the bio-information estimation model is valid by using at least one of a change in shape of the residual spectra over time and magnitude of vectors representing the residual spectra.

The processor may be further configured to: extract updated principal component spectra from the in vivo updating spectra and the training in vivo spectra; update a first bio-information estimation model for estimating a variation of bio-information compared to reference bio-information based on the updated principal component spectra; and update a second bio-information estimation model for estimating bio-information based on the reference bio-information and the estimated variation of bio-information compared to the reference bio-information.

The reference bio-information of the updated second bio-information estimation model may be determined from a combination of first spectra measured from a subject when the subject is on an empty stomach, and second spectra measured from the subject immediately before the bio-information estimation model is determined as not being valid.

The reference bio-information of the updated second bio-information estimation model may be determined based on an average of the first spectra and the second spectra.

The processor may be further configured to obtain bio-information based on the updated bio-information estimation model, and the bio-information may be a concentration of at least one of glucose, triglyceride, urea, uric acid, lactate, protein, cholesterol, antioxidant, and ethanol.

The bio-information estimation model may be generated using a net analyte signal (NAS) algorithm.

The processor may be further configured to receive the in vivo updating spectra from an external device.

The apparatus may further include a spectrometer configured to emit the in vivo updating spectra by emitting light onto an object and receiving the light reflected or scattered from the object.

According to an aspect of an example embodiment, there is provided a method of updating a bio-information estimation model, the method including: determining validity of a bio-information estimation model; in response to the bio-information estimation model not being valid, obtaining in vivo updating spectra which are measured starting when the bio-information estimation model is determined as not being valid; and updating the bio-information estimation model based on the in vivo updating spectra, and training in vivo spectra that are used for generating the bio-information estimation model.

The determining the validity of the bio-information estimation model may include: obtaining in vivo estimation spectra; obtaining residual spectra from the in vivo estimation spectra; and determining the validity of the bio-information estimation model by analyzing the residual spectra.

The determining the validity of the bio-information estimation model may include determining the validity of the bio-information estimation model based on at least one of a change in shape of the residual spectra over time and magnitude of vectors representing the residual spectra.

The updating the bio-information estimation model may include: extracting updated principal component spectra from the in vivo updating spectra and the training in vivo spectra; updating a first bio-information estimation model for estimating a variation of bio-information compared to reference bio-information based on the updated principal component spectra; and updating a second bio-information estimation model for estimating bio-information based on the reference bio-information and the estimated variation of bio-information compared to the reference bio-information.

The reference bio-information of the updated second bio-information estimation model may be determined based on a combination of first spectra measured from a subject when the subject is on an empty stomach, and second spectra measured from the subject immediately before the bio-information estimation model is determined as not being valid.

The reference bio-information of the updated second bio-information estimation model may be determined based on an average of the first spectra and the second spectra.

The method may further include obtaining bio-information based on the updated bio-information estimation model, and the bio-information may be a concentration of at least one of glucose, triglyceride, urea, uric acid, lactate, protein, cholesterol, antioxidant, and ethanol.

The bio-information estimation model may be generated using a net analyte signal (NAS) algorithm.

The obtaining the in vivo updating spectra may include obtaining the in vivo updating spectra by receiving the in vivo updating spectra from an external device.

The obtaining the in vivo updating spectra may include obtaining the in vivo updating spectra by emitting light onto an object and receiving the light reflected or scattered from the object.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
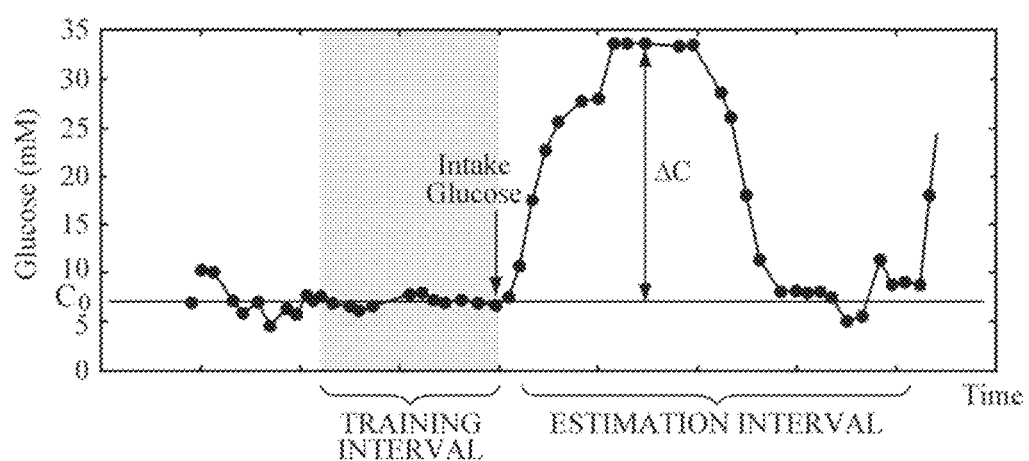
FIGS. 1 and 2 are diagrams explaining a concept of a Net Analyte Signal (NAS) algorithm.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

It will be understood that, although the terms first, second, etc. may b used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Components that will be described in the specification are discriminated merely according to functions mainly performed by the components. That is, two or more components which will be described later can be integrated into a single component. Furthermore, a single component can be separated into two or more components. Moreover, each component can additionally perform some or all of a function executed by another component in addition to the main function thereof. Some or all of the main function of each component can be carried out by another component. Each component may be implemented in hardware or software, or a combination thereof.

Figure 2:
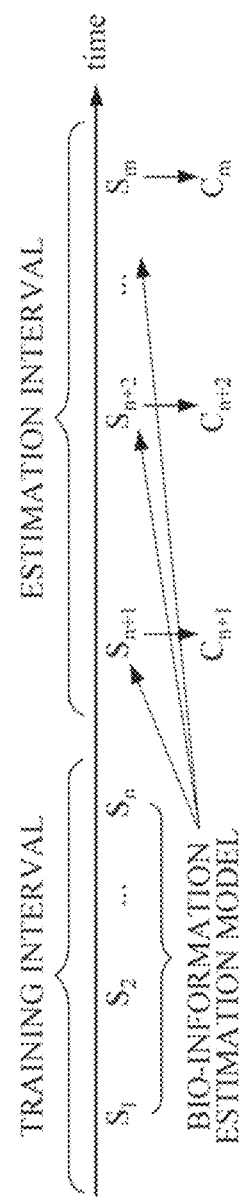

FIGS. 1 and 2 are diagrams explaining a concept of a Net Analyte Signal (NAS) algorithm.

Referring to FIGS. 1 and 2, a processor may use the Net Analyte Signal (NAS) algorithm to generate a bio-information estimation model by learning a spectrum change factor, which causes a spectrum to be changed and is irrelevant to a change in bio-information. The processor may use in vivo spectra $S_1, S_2, \ldots,$ and $S_n$ measured in a training interval as training data. Further, the processor may use the NAS algorithm to estimate bio-information $C_{n+1}, C_{n+2}$ and $C_m$ based on in vivo spectra $S_{n+1}, S_{n+2}, \ldots,$ and $S_m$, measured in an estimation interval after the training interval, and the generated bio-information estimation model. The in vivo spectra $S_1, S_2, \ldots,$ and $S_n$ may be referred to as training in vivo spectra, and the in vivo spectra $S_{n+1}, S_{n+2}, \ldots,$ and $S_m$ may be referred to as in vivo estimation spectra. The training interval may be a time interval or time period during which bio-information does not practically change or a change in the bio-information is less than a predetermined threshold value. If the bio-information is information about glucose, the training interval may be set to a fasting period. Line C may denote a glucose concentration level, or an average value of the in vivo spectra $S_1, S_2, \ldots,$ and $S_n$ in the fasting interval. AC may denote an increment in blood glucose levels compared to fasting blood glucose levels.

That is, the processor may use the NAS algorithm to generate the bio-information estimation model based on the in vivo spectra measured in the training interval, and then to estimate bio-information by applying the generated bio-information estimation model to the estimation interval. Accordingly, in the case where at least one of spectrum change factors, which are irrelevant to bio-information, is changed at any one time during the estimation interval due to factors, such as a change in temperature of an object, a change in pressure between an object and an apparatus, and the like, an error in estimating bio-information may increase as residual increases from that time. A residual spectrum may indicate a difference between an in vivo spectrum, which is reconstructed using a bio-information estimation model, and an actually measured in vivo spectrum.

Figure 3:
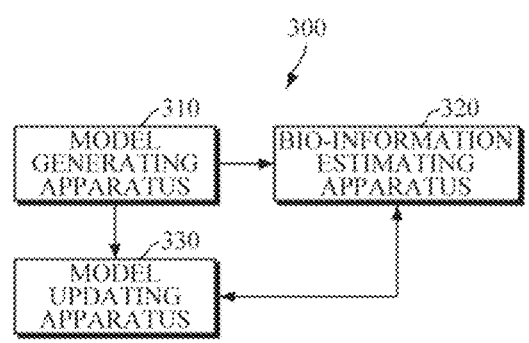
FIG. 3 is a diagram illustrating an example of a bio-information measuring apparatus.
Figure 4:
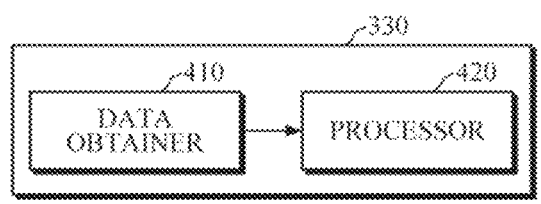
FIG. 4 is a diagram illustrating an example of a model updating apparatus.

FIG. 3 is a diagram illustrating an example of a bio-information measuring apparatus, and FIG. 4 is a diagram illustrating an example of a model updating apparatus. The bio-information measuring apparatus 300 of FIG. 3 is an apparatus for measuring bio-information of an object by analyzing an in vivo spectrum of the object, and may be embedded in an electronic device or may be enclosed in a housing to be provided as a separate device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Here, the bio-information is the concentration of an analyte, and examples of the analyte may include, but is not limited to, glucose, triglyceride, urea, uric acid, lactate, protein, cholesterol, antioxidant (e.g., vitamin, carotenoid, flavonoid, ascorbic acid, tocopherol, etc.) ethanol, and the like. In addition, in the case where an in vivo analyte is glucose, bio-information may indicate blood glucose. Hereinafter, description will be given of an embodiment in which bio-information is blood glucose for convenience of explanation.

Referring to FIG. 3, a bio-information measuring apparatus 300 includes a model generating apparatus 310, a bio-information estimating apparatus 320, and a model updating apparatus 330. Here, the model generating apparatus 310, the bio-information estimating apparatus 320, and the model updating apparatus 330 may be implemented as separate hardware devices (e.g., separate plural processors), or may be implemented in a single hardware device (e.g., a single processor).

The model generating apparatus 310 may generate a bio-information estimation model.

The model generating apparatus 310 may obtain in vivo spectra (hereinafter referred to as in vivo training spectra), which are measured in an interval (e.g., fasting interval) in which blood glucose of an object does not practically change or the change in blood glucose is lower than a threshold change value. In this case, the in vivo spectrum may be an absorption spectrum, a reflectance spectrum, or a transmittance spectrum.

In one embodiment, the model generating apparatus 310 may obtain the in vivo training spectra by receiving the in vivo training spectra from an external device which measures and/or stores in vivo training spectra. In this case, the model generating apparatus 310 may communicate with the external device by using wired or wireless communication techniques. Examples of the wireless communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like, but the communication techniques are not limited thereto.

In another embodiment, the model generating apparatus 310 may obtain the in vivo training spectra by emitting light onto an object and receiving light reflected or scattered from the object. In this case, the model generating apparatus 310 may measure the in vivo training spectra by using Infrared spectroscopy or Raman spectroscopy, but is not limited thereto, and may measure the in vivo spectra by using various other spectroscopic methods. To this end, the model generating apparatus 310 may include a light source which emits light onto an object, and a photodetector which measures in vivo spectra by receiving light reflected or scattered from the object. The light source may emit near infrared (NIR) light or mid infrared (MIR) light. However, wavelengths of light to be emitted by the light source may vary according to a purpose of measurement or the types of an analyte. Further, the light source is not necessarily a single light-emitting body, and may be formed of an array of a plurality of light-emitting bodies. The light source may include a light emitting diode (LED), a laser diode, a phosphor, and the like. The photodetector may include a photo diode, a photo transistor (PTr), an image sensor (e.g., a charge-coupled device (CCD), a Complementary Metal Oxide Semiconductor (CMOS), etc.), and the like. The photodetector is not necessarily a single device, and may be formed of an array of a plurality of devices. There may be various numbers and arrangements of light sources and photodetectors, and the number and arrangement thereof may vary according to the types and a purpose of use of bio-information, the size and shape of an electronic device in which the model generating apparatus 310 is embedded, and the like.

The model generating apparatus 310 may generate a bio-information estimation model based on the in vivo training spectra, and may transmit the generated bio-information estimation model to the bio-information estimating apparatus 320. In one embodiment, upon obtaining the in vivo training spectra, the model generating apparatus 310 may generate a bio-information estimation model based on the obtained in vivo training spectra. For example, the model generating apparatus 310 may generate the bio-information estimation model based on the obtained in vivo training spectra and the NAS algorithm. More specifically, the model generating apparatus 310 may learn a spectrum change factor, which is irrelevant to a change in bio-information, based on the in vivo training spectra measured in the fasting interval as training data. In this case, the model generating apparatus 310 may extract principal component spectra from the in vivo training spectra, which are measured in the fasting interval, by using various dimension reduction algorithms such as Principal Component Analysis (PCA), Independent Component Analysis (ICA), Non-negative Matrix Factorization (NMF), Singular Value Decomposition (SVD), and the like. Further, the model generating apparatus 310 may generate the bio-information estimation model based on the learning result, i.e., the extracted principal component spectra. In this case, the generated bio-information estimation model may include: a first bio-information estimation model for estimating a variation of blood glucose compared to a fasting blood glucose level based on the extracted principal component spectra; and a second bio-information estimation model for estimating blood glucose based on the fasting blood glucose level and the estimated variation of blood glucose compared to the fasting blood glucose level. The first bio-information estimation model and the second bio-information estimation model may be represented by the following Equations 1 and 2 respectively.

$$\begin{bmatrix} C_1 \\ C_2 \\ \vdots \\ C_k \\ \Delta C_g \end{bmatrix} = \begin{bmatrix} PC_1 \\ PC_2 \\ \vdots \\ PC_k \\ \varepsilon_g \end{bmatrix}^{-1} \times S_{skin}/L \qquad \text{[Equation 1]}$$

$$C_g = \Delta C_g + C_{g0} \quad \text{[Equation 2]}$$

Herein, $C_1$, $C_2$, and $C_k$ denote the concentrations of principal components; $\Delta C_g$ denotes an increment in blood glucose levels compared to the fasting blood glucose level; $PC_1$, $PC_2$, and $PC_k$ denote vectors representing principal component spectra; $\varepsilon_g$ denotes a vector representing a spectrum of glucose per unit concentration (e.g., 1 mM) (hereinafter referred to as a pure component spectrum); L denotes a light path length; k denotes a number of principal components; $C_g$ denotes an estimated blood glucose level; and $C_{g0}$ denotes the fasting blood glucose level. $\varepsilon_g$ may be obtained experimentally and stored in the bio-information measuring apparatus 300 as a predetermined value. $S_{skin}$ denotes a vector representing the in vivo estimation spectrum.

The bio-information estimating apparatus 320 may obtain an in vivo spectrum of the object which is measured for estimating bio-information (hereinafter referred to as an in vivo estimation spectrum).

In one embodiment, the bio-information estimating apparatus 320 may obtain in vivo estimation spectra by receiving the in vivo estimation spectra from an external device which measures and/or stores in vivo estimation spectra. In this case, the bio-information estimating apparatus 320 may communicate with the external device by using wired or wireless communication techniques.

In another embodiment, the bio-information estimating apparatus 320 may obtain the in vivo estimation spectra by emitting light onto an object and receiving light reflected or scattered from the object. To this end, the bio-information estimating apparatus 320 may include a light source and a photodetector.

The bio-information estimating apparatus 320 may estimate a blood glucose level of the object and a concentration of the principal component based on the obtained in vivo estimation spectra, and the bio-information estimation model that is received from the model generating apparatus 310. For example, the bio-information estimating apparatus 320 may estimate the blood glucose level of the object and the concentration of the principal component by using the above Equations 1 and 2.

The bio-information estimating apparatus 320 may transmit, to the model updating apparatus 330, the in vivo estimation spectra, and the blood glucose level and the concentration of the principal component which are estimated using the in vivo estimation spectra and the bio-information estimation model.

The model updating apparatus 330 determines validity of a bio-information estimation model; and if the bio-information estimation model is not valid, the model updating apparatus 330 may update the bio-information estimation model. As illustrated in FIG. 4, the model updating apparatus 330 includes a data obtainer 410 and a processor 420.

The data obtainer 410 may obtain in vivo spectra, which are measured during a predetermined period of time from a time when it is determined that the bio-information estimation model is not valid (hereinafter referred to as in vivo updating spectra). In one embodiment, the data obtainer 410 may obtain in vivo updating spectra by receiving the in vivo updating spectra from an external device which measures and/or stores in vivo updating spectra. In this case, the data obtainer 410 may be implemented by a communication interface, a communication module, a WiFi module, or the like, and the bio-information estimating apparatus 320 may communicate with the external device using wired or wireless communication techniques. In another embodiment, the bio-information estimating apparatus 320 may obtain the in vivo updating spectra by emitting light onto an object and receiving light reflected or scattered from the object. To this end, the data obtainer 410 may include a light source and a photodetector, and may be implemented as a spectrometer, an optical sensor, or the like.

Further, the data obtainer 410 may obtain, from the bio-information estimating apparatus 320, the in vivo estimation spectra, and the blood glucose level and the concentration of the principal component which are estimated using the in vivo estimation spectra and the bio-information estimation model. In this case, the data obtainer 410 may obtain the information using wired or wireless communication techniques.

The processor 420 may control the overall operation of the model updating apparatus 330.

The processor 420 may determine the validity of the bio-information estimation model.

Upon obtaining the in vivo estimation spectra, and the blood glucose level and the concentration of the principal component which are estimated based on the in vivo estimation spectra and the bio-information estimation model, the processor 420 may obtain a residual spectrum of the in vivo estimation spectrum based on the in vivo estimation spectrum, the blood glucose level, and the concentration of the principal component. For example, the processor 420 may reconstruct the in vivo estimation spectrum based on the in vivo estimation spectrum, the blood glucose level, and the concentration of the principal component by using the following Equation 3, and may obtain the residual spectrum of the obtained in vivo estimation spectrum by using the following Equation 4.

$$S_{recon} = \begin{bmatrix} PC_1 \\ PC_2 \\ \vdots \\ PC_k \\ \varepsilon_g \end{bmatrix} \times \begin{bmatrix} C_1 \\ C_2 \\ \vdots \\ C_k \\ \Delta C_g \end{bmatrix} \times L \quad \text{[Equation 3]}$$

$$S_{residual} = S_{skin} - S_{recon} \quad \text{[Equation 4]}$$

Herein, $S_{recon}$ denotes a vector representing the reconstructed in vivo estimation spectrum (e.g., a reconstructed in vivo estimation spectrum at an actual blood glucose estimation time); $PC_1$, $PC_2$, and $PC_k$ denote vectors representing principal component spectra used for generating the bio-information estimation model; denotes a vector representing a pure component spectrum used for generating the bio-information estimation model; $C_1$, $C_2$, and $C_k$ denote the concentrations of the principal components; $\Delta C_g$ denotes an increment in blood glucose levels compared to a fasting blood glucose level; L denotes a light path length; $S_{skin}$ denotes a vector representing the in vivo estimation spectrum (e.g., an in vivo estimation spectrum at a specific reference time); and $S_{residual}$ denotes a vector representing the residual spectrum of $S_{skin}$.

The above description is given of the embodiment in which the processor 420 obtains, from the bio-information estimating apparatus 320, the in vivo estimation spectrum, and the blood glucose level and the concentration of the principal component which are estimated based on the in vivo estimation spectrum and the bio-information estimation model, and obtains the residual spectrum of the in vivo estimation spectrum based on the obtained information, but the processor 420 is not limited thereto. That is, the processor 420 may obtain the in vivo estimation spectrum, may estimate the blood glucose level and the concentration of the principal component based on the obtained in vivo estimation spectrum and the bio-information estimation model, and then may obtain the residual spectrum of the in vivo estimation spectrum based on the estimation.

The processor 420 may determine the validity of the bio-information estimation model by analyzing the residual spectrum of the in vivo estimation spectrum.

In one embodiment, the processor 420 may determine the validity of the bio-information estimation model by monitoring a change in shape of the residual spectrum over time. For example, the processor 420 may select one or more previous residual spectra as reference residual spectra, and may determine a change in shape of the residual spectra over time based on similarity between the selected reference residual spectra and a currently obtained residual spectrum. In this case, the previous residual spectra may be residual spectra of previously measured in vivo estimation spectra, which are measured before the in vivo estimation spectra are measured. Further, upon determining the change in shape of the residual spectra over time, if a shape variation exceeds a predetermined first reference value, the processor 420 may determine that the bio-information estimation model is not valid. For example, if similarity between the reference residual spectra and the residual spectra of the in vivo estimation spectra is less than a second reference value, which corresponds to the predetermined first reference value, the processor 420 may determine that the bio-information estimation model is not valid. In this case, the processor 420 may use various similarity calculation algorithms such as Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

In another embodiment, the processor 420 may determine the validity of the bio-information estimation model based on a magnitude of a residual spectrum vector which corresponds to the residual spectrum. For example, if the magnitude of the residual spectrum vector is greater than a predetermined reference value, the processor 420 may determine that the bio-information estimation model is not valid.

In yet another embodiment, the processor may determine the validity of the bio-information estimation model by considering both the change in shape of the residual spectra over time and the magnitude of the residual spectrum vector.

Upon determining that the bio-information estimation model is not valid, the processor 420 may control the data obtainer 410 to obtain a plurality of in vivo updating spectrum, which are measured during a predetermined period of time from a time when it is determined that the bio-information estimation model is not valid.

The processor 420 may update the bio-information estimation model by using the obtained plurality of in vivo updating spectra, and the in vivo spectra (in vivo training spectra and in vivo updating spectra) used for generating/updating the bio information estimation model. For example, the processor 420 may extract updated principal component spectra from the plurality of in vivo updating spectra and all the in vivo spectra used for generating/updating the bio-information estimation model, and may update the bio-information estimation model based on the updated principal component spectra. The updated bio-information estimation model may include: a first bio-information estimation model for estimating a variation of blood glucose compared to a reference blood glucose level based on the updated principal component spectra; and a second bio-information estimation model for estimating blood glucose based on the reference blood glucose level and the estimated variation of blood glucose compared to the reference blood glucose level. The first bio-information estimation model and the second bio-information estimation model may be represented by the following Equations 5 and 6 respectively, and the reference blood glucose level may be represented by the following Equation 7.

$$\begin{bmatrix} C'_1 \\ C'_2 \\ \vdots \\ C'_k \\ \Delta C'_g \end{bmatrix} = \begin{bmatrix} PC'_1 \\ PC'_2 \\ \vdots \\ PC'_k \\ \varepsilon_g \end{bmatrix} \times \frac{S_{skin}}{L} \qquad \text{[Equation 5]}$$

$$C_g = \Delta C'_g + C'_{g0} \qquad \text{[Equation 6]}$$

$$C'_{g0} = \frac{C_{g0} + C_{g1} + \ldots + C_{gn}}{n} \qquad \text{[Equation 7]}$$

Herein, $C'_1$, $C'_2$, and $C'_k$ denote the concentrations of the updated principal components; $\Delta C'_g$ denotes the variation of blood glucose compared to the reference blood glucose level; $PC'_1$, $PC'_2$, and $PC'_k$ denote the updated principal component spectrum vectors; $\varepsilon_g$ denotes a vector representing a spectrum of glucose per unit concentration (e.g., 1 mM) (hereinafter referred to as a pure component spectrum); L denotes a light path length; k denotes a number of principal components; $C_g$ denotes an estimated blood glucose level; $C'_{g0}$ denotes the reference blood glucose level; $C_{g0}$ denotes the fasting blood glucose level; $C_{g1}$ and $C_{gn}$ denote blood glucose levels estimated immediately before it is determined that the bio-information estimation model is not valid; and n denotes a number of times of updating the bio-information estimation model.

The processor 420 may transmit the updated bio-information estimation model to the bio-information estimating apparatus 320. In this case, the bio-information estimating apparatus 320 may receive the updated bio-information estimation model for use in estimating bio-information.

Figure 5:
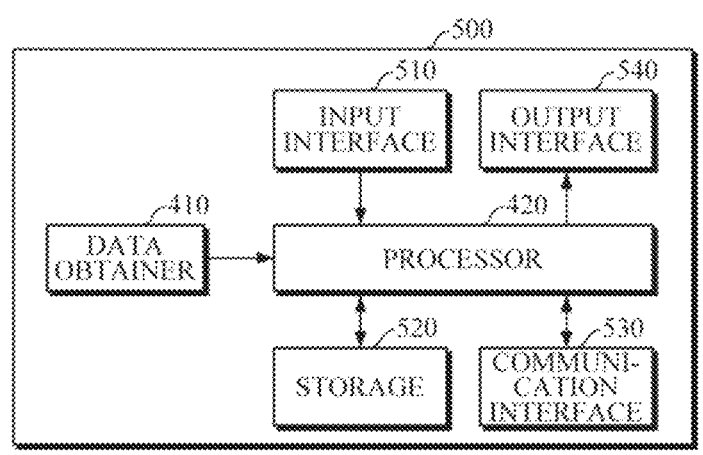
FIG. 5 is a diagram illustrating another example of a model updating apparatus.

FIG. 5 is a diagram illustrating another example of a model updating apparatus. The model updating apparatus 500 of FIG. 5 may be another example of the model updating apparatus 330 of FIG. 3.

Referring to FIG. 5, the model updating apparatus 500 includes the data obtainer 410, the processor 420, an input interface 510, a storage 520, a communication interface 530, and an output interface 540. Here, the data obtainer 410 and the processor 420 are described above with reference to FIG. 4, such that detailed description thereof will be omitted.

The input interface 510 may receive input of various operation signals from a user. In one embodiment, the input interface 510 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 520 may store programs or commands for operation of the model updating apparatus 500, data input to the model updating apparatus 500, and processing result data of the model updating apparatus 500. In addition, the storage 520 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the model updating apparatus 500 may operate an external storage medium, such as web storage and the like, which performs a storage function of the storage 520 on the Internet. The storage 520 may store the bio-information estimation model, the first bio-information estimation model, and the second bio-information estimation model.

The communication interface 530 may perform communication with an external device. For example, the communication interface 530 may transmit, to the external device, the data input to the model updating apparatus 500, the data stored in and processed by the model updating apparatus 500, and the like, or may receive, from the external device, various data useful for determining the validity of the bio-information estimation model.

In this case, the external device may be medical equipment using the data input to the model updating apparatus 500, the data stored in and processed by the model updating apparatus 500, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 530 may communicate with an external device by using wired or wireless communication techniques. In this case, examples of the wireless communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 540 may output the data input to the model updating apparatus 500, the data stored in and processed by the model updating apparatus 500, and the like. In one embodiment, the output interface 540 may output the data input to the model updating apparatus 500, the data stored in and processed by the model updating apparatus 500, and the like, by using at least one of an acoustic method, a visual method, and a tactile method. To this end, the output interface 540 may include a display, a speaker, a vibrator, and the like.

Figure 6:
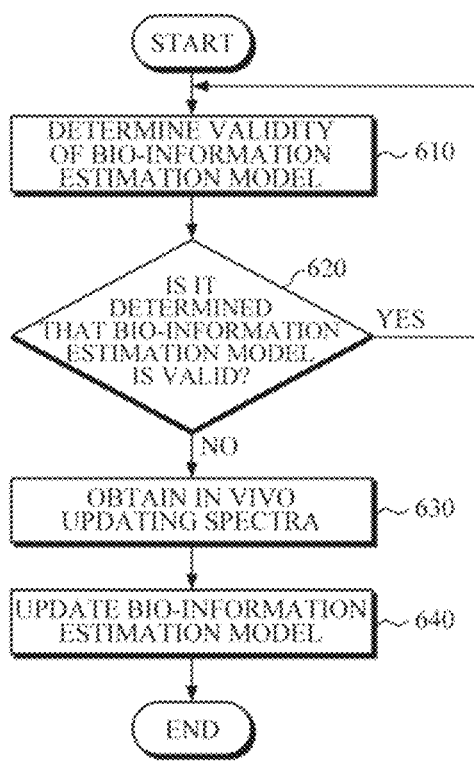
FIG. 6 is a diagram illustrating an example of a method of updating a bio-information estimation model.

FIG. 6 is a diagram illustrating an example of a method of updating a bio-information estimation model. The method of updating bio-information estimation model of FIG. 6 may be performed by the model updating apparatuses 330 and 500 of FIGS. 3 and 5.

Referring to FIG. 6, the model updating apparatus may determine the validity of a bio-information estimation model in operation 610. For example, the model updating apparatus may obtain in vivo estimation spectra, may obtain residual spectra of the in vivo estimation spectra, and may determine the validity of the bio-information estimation model based on at least one of a change in shape of the obtained residual spectra over time and magnitude of vectors which represent the obtained residual spectra. The residual spectra may be obtained by subtracting a reconstructed in vivo estimation spectrum from a vector representing an estimated vivo estimation spectrum. In this case, the model updating apparatus may obtain the residual spectra of the in vivo estimation spectra by using the above Equations 3 and 4.

Upon determining that the bio-information estimation model is not valid in operation 620, the model updating apparatus may obtain in vivo updating spectra in operation 630, which are measured during a predetermined period of time from a time when it is determined that the bio-information estimation model is not valid. For example, the model updating apparatus may obtain the in vivo updating spectra by receiving the in vivo updating spectra from an external device, or may obtain the in vivo updating spectra by emitting light onto an object and receiving light reflected or scattered from the object.

The model updating apparatus may update the bio-information estimation model by using the obtained in vivo updating spectra and the in vivo spectra used for generating the bio-information estimation model in operation 640. For example, the model updating apparatus may extract updated principal component spectra from the in vivo updating spectra and the in vivo spectra used for generating the bio-information estimation model, and may update the bio-information estimation model based on the updated principal component spectra. In this case, the bio-information estimation model may include a first bio-information estimation model for estimating a variation of blood glucose compared to a reference blood glucose level based on the updated principal component spectra; and a second bio-information estimation model for estimating blood glucose based on the reference blood glucose level and the estimated variation of blood glucose compared to the reference blood glucose level. The first bio-information estimation model and the second bio-information estimation model may be represented by the above Equations 5 and 6 respectively, and the reference blood glucose level may be represented by the above Equation 7.

Figure 7:
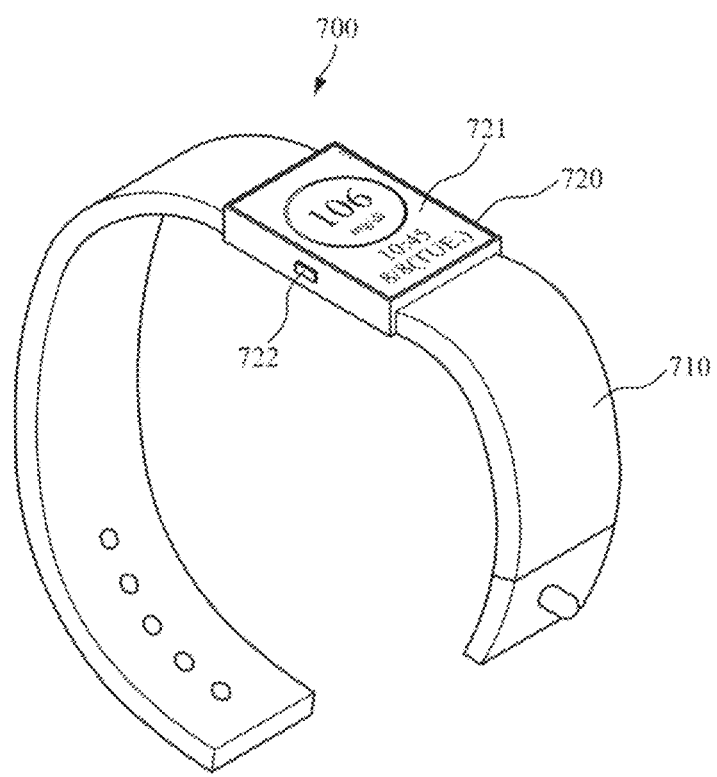
FIG. 7 is a diagram illustrating an example of a wrist-type wearable device.

FIG. 7 is a diagram illustrating an example of a wrist-type wearable device.

Referring to FIG. 7, the wrist-type wearable device 700 includes a strap 710 and a main body 720.

The strap 710 may be connected to both ends of the main body 720 so as to be fastened in a detachable manner or may be integrally formed therewith as a smart band. The strap 710 may be made of a flexible material to be wrapped around a user's wrist so that the main body 720 may be worn on the wrist.

The wrist-type wearable device 700, the bio-information measuring apparatus 300, the model generating apparatus 310, the bio-information estimating apparatus 320, and/or the model updating apparatuses 330 and 500, which are described above, may be mounted in the main body 720. Further, the main body 720 may include a battery which supplies power to wrist-type wearable device 700, the bio-information measuring apparatus 300, the model generating apparatus 310, the bio-information estimating apparatus 320, and the model updating apparatuses 330 and 500.

An optical sensor may be mounted at the bottom of the main body 720 to be exposed to a user's wrist. Accordingly, when a user wears the wrist-type wearable device 700, the optical sensor may naturally come into contact with the user's skin. In this case, the optical sensor may obtain in vivo spectra by emitting light onto an object and receiving light reflected or scattered from the object.

The wrist-type wearable device 700 may further include a display 721 and an input interface 722 which are mounted at the main body 720. The display 721 may display data processed by the wrist-type wearable device 700, the bio-information measuring apparatus 300, the model generating apparatus 310, the bio-information estimating apparatus 320, and the model updating apparatuses 330 and 500, processing result data thereof, and the like. The input interface 722 may receive various operation signals from a user.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for updating a bio-information estimation model, the apparatus comprising:
   a memory configured to store the bio-information estimation model; and
   a processor configured to determine whether the bio-information estimation model is valid, obtain in vivo updating spectra which are measured starting when the bio-information estimation model is determined as not being valid, update the bio-information estimation model based on the in vivo updating spectra, and training in vivo spectra that are used for generating the bio-information estimation model.

2. The apparatus of claim 1, further comprising
   a spectrometer configured to measure in vivo estimation spectra,
   wherein the processor is further configured to obtain residual spectra from the in vivo estimation spectra, and determine whether the bio-information estimation model is valid by analyzing the residual spectra.

3. The apparatus of claim 2, wherein the processor is further configured to determine whether the bio-information estimation model is valid by using at least one of a change in shape of the residual spectra over time and magnitude of vectors representing the residual spectra.

4. The apparatus of claim 1, wherein the processor is further configured to:
   extract updated principal component spectra from the in vivo updating spectra and the training in vivo spectra;
   update a first bio-information estimation model for estimating a variation of bio-information compared to reference bio-information based on the updated principal component spectra; and
   update a second bio-information estimation model for estimating bio-information based on the reference bio-information and the estimated variation of bio-information compared to the reference bio-information.

5. The apparatus of claim 4, wherein the reference bio-information of the updated second bio-information estimation model is determined from a combination of first spectra measured from a subject when the subject is on an empty stomach, and second spectra measured from the subject immediately before the bio-information estimation model is determined as not being valid.

6. The apparatus of claim 5, wherein the reference bio-information of the updated second bio-information estimation model is determined based on an average of the first spectra and the second spectra.

7. The apparatus of claim 1, wherein the processor is further configured to obtain bio-information based on the updated bio-information estimation model, and the bio-information is a concentration of at least one of glucose, triglyceride, urea, uric acid, lactate, protein, cholesterol, antioxidant, and ethanol.

8. The apparatus of claim 1, wherein the bio-information estimation model is generated using a net analyte signal algorithm.

9. The apparatus of claim 1, wherein the processor is further configured to receive the in vivo updating spectra from an external device.

10. The apparatus of claim 1, further comprising a spectrometer configured to emit the in vivo updating spectra by emitting light onto an object and receiving the light reflected or scattered from the object.

11. A method of updating a bio-information estimation model, the method comprising:
    determining validity of a bio-information estimation model;
    in response to the bio-information estimation model not being valid, obtaining in vivo updating spectra which are measured starting when the bio-information estimation model is determined as not being valid; and
    updating the bio-information estimation model based on the in vivo updating spectra, and training in vivo spectra that are used for generating the bio-information estimation model.

12. The method of claim 11, wherein the determining the validity of the bio-information estimation model comprises:
    obtaining in vivo estimation spectra;
    obtaining residual spectra from the in vivo estimation spectra; and
    determining the validity of the bio-information estimation model by analyzing the residual spectra.

13. The method of claim 12, wherein the determining the validity of the bio-information estimation model comprises determining the validity of the bio-information estimation model based on at least one of a change in shape of the residual spectra over time and magnitude of vectors representing the residual spectra.

14. The method of claim 11, wherein the updating the bio-information estimation model comprises:
    extracting updated principal component spectra from the in vivo updating spectra and the training in vivo spectra;
    updating a first bio-information estimation model for estimating a variation of bio-information compared to reference bio-information based on the updated principal component spectra; and updating a second bio-information estimation model for estimating bio-information based on the reference bio-information and the estimated variation of bio-information compared to the reference bio-information.

15. The method of claim 14, wherein the reference bio-information of the updated second bio-information estimation model is determined based on a combination of first spectra measured from a subject when the subject is on an empty stomach, and second spectra measured from the subject immediately before the bio-information estimation model is determined as not being valid.

16. The method of claim 15, wherein the reference bio-information of the updated second bio-information estimation model is determined based on an average of the first spectra and the second spectra.

17. The method of claim 11, further comprising obtaining bio-information based on the updated bio-information estimation model, and the bio-information is a concentration of at least one of glucose, triglyceride, urea, uric acid, lactate, protein, cholesterol, antioxidant, and ethanol.

18. The method of claim 11, wherein the bio-information estimation model is generated using a net analyte signal algorithm.

19. The method of claim 11, wherein the obtaining the in vivo updating spectra comprises obtaining the in vivo updating spectra by receiving the in vivo updating spectra from an external device.

20. The method of claim 11, wherein the obtaining the in vivo updating spectra comprises obtaining the in vivo updating spectra by emitting light onto an object and receiving the light reflected or scattered from the object.

* * * * *